United States Patent [19]
Hirano et al.

[11] Patent Number: 6,020,363
[45] Date of Patent: Feb. 1, 2000

[54] ISOCOUMARIN DERIVATIVES AND USE THEREOF IN DRUGS

[75] Inventors: Shin-ichi Hirano, Chigasaki; Toshiyuki Mase, Iwata; Naoki Agata, Fujisawa; Hiroshi Iguchi; Naoki Matsumoto, both of Yokohama; Takeo Yoshioka, Ayase; Hiroshi Tone, Yokohama; Hiroyuki Kumagai, Chigasaki; Masaaki Ishizuki, Mishima; Tomio Takeuchi, Tokyo, all of Japan

[73] Assignees: Mercian Corporation; Zaidan Hojin Biseibutsu Kagaku Kenkyu Kai, both of Japan

[21] Appl. No.: 09/202,606

[22] PCT Filed: Jun. 17, 1996

[86] PCT No.: PCT/JP96/01657

§ 371 Date: Dec. 17, 1998

§ 102(e) Date: Dec. 17, 1998

[87] PCT Pub. No.: WO97/48693

PCT Pub. Date: Dec. 24, 1997

[51] Int. Cl.[7] .......................... A61K 31/35; C07D 311/76
[52] U.S. Cl. ............................. 514/456; 549/289
[58] Field of Search .............................. 549/289; 514/456

[56] References Cited

U.S. PATENT DOCUMENTS 5,096,924   3/1992   Ishizuka et al. .................... 514/456

FOREIGN PATENT DOCUMENTS

| 3-2177 | 1/1991 | Japan . |
|---|---|---|
| 4-112884 | 4/1992 | Japan . |
| 5-97841 | 4/1993 | Japan . |
| 6-183966 | 7/1994 | Japan . |

OTHER PUBLICATIONS

Yamazaki et al., *Chem. Pharm. Bull.*, 20(10), 2276–2278 (1972).

*Primary Examiner*—Fiona T. Powers
*Attorney, Agent, or Firm*—Wenderoth, Lind & Ponack, L.L.P.

[57] ABSTRACT

Compounds of the formula (I)

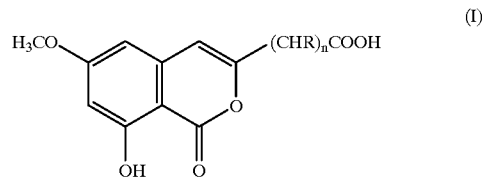

wherein R is a hydrogen atom or a $C_{1-6}$ alkyl group and n is an integer of 0 or 1, and pharmaceutical preparations thereof are provided. These pharmaceutical preparations are useful for the prevention or treatment of diseases associated with an abnormality in immunological regulatory function or vascularization.

10 Claims, 2 Drawing Sheets

ISOCOUMARIN DERIVATIVES AND USE THEREOF IN DRUGS

TECHNICAL FIELD

This invention relates to isocoumarin derivatives and their use in medicines. More particularly, it relates to the use of isocoumarin derivatives for the prevention or treatment of diseases associated with an abnormality in immunological regulatory function or vascularization.

BACKGROUND ART

An isocoumarin derivative, particularly 3-hydroxymethyl-6-methoxy-8-hydroxy-1H-2-benzopyran-1-one represented by the formula

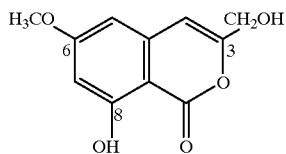

was first found as a compound produced by *Streptoverticillium eurocidicum*, and has attracted attention under the name of the antibiotic MI43-37F11 because of its growth-inhibiting activity against various animal cells and human cancer cells (Japanese Patent Laid-Open No. 2177/'91). Subsequently, investigations have been made on the method for the chemical synthesis of the aforesaid antibiotic MI43-37F11 (hereinafter abbreviated as MI43). As a result, isocoumarin derivatives having a leaving group-containing methyl group (e.g., halomethyl) or benzyloxymethyl at the 3-position of an isocoumarin skeleton have been provided as intermediates (Japanese Patent Laid-Open No. 112884/'92), and isocoumarin derivatives having, at the aforesaid 3-position, a group of the formula

wherein $R_3$ and $R_4$ are each independently a substituted or unsubstituted alkyl group, an alkoxy group, an alkanoyloxy group, a mono- or di-substituted amino group, a phenylthio group or $N_3$, have been provided as compound having a pharmacological activity similar to that of MI43 (Japanese Patent Laid-Open No. 97841/'93).

On the other hand, the use of MI43 as an immunological regulator has been proposed because its oral administration can significantly inhibit adjuvant arthritis in rats and collagen-induced arthritis in mice (Japanese Patent Laid-Open No. 183966/'94). Although MI43 is considerably effective as an immunological regulator, there would still remain a need for the provision of a more effective compound or medicine.

In the case of drugs conventionally used for the treatment of autoimmune diseases, such as steroid hormones, gold preparations, D-penicillamine, levamisole and salazosulfapyridine, strict restrictions are encountered in using them, because they may sometimes produce serious side effects such as adrenal dysfunction, infection, renal disorders, hematopoietic disorders and gastrointestinal disorders.

Under the above-described background, an object of the present invention is to provide pharmaceutical preparations having no appreciable side effects and exhibiting excellent efficacy (in particular, bioavailability) in mammals including human beings.

DISCLOSURE OF THE INVENTION

In order to accomplish the above object, the present inventors have made investigations on the pharmacological effects and bioavailability of various isocoumarin derivatives. As a result, it has been found that isocoumarin derivatives having a carboxyl group attached to the 3-position, either directly or via a methylene or methine group, instead of the hydroxymethyl group attached to the 3-position of MI43, have an immunological regulatory effect equal or superior to that of, for example, MI43 and also have low toxicity and very excellent bioavailability. Moreover, it has also been found that, when administered orally to mammals, the compounds having such properties surprisingly exhibit high in vivo stability. Furthermore, it has also been found that the aforesaid compounds can significantly inhibit vascularization in mammals. The aforesaid isocoumarin derivatives having a carboxyl group attached to the 3-position via a methylene or methine group are compounds which have not been described in the literature of the prior art.

Accordingly, the present invention provides a pharmaceutical preparation comprising a pharmaceutically acceptable additive and a pharmacologically effective amount of a compound of the formula (I)

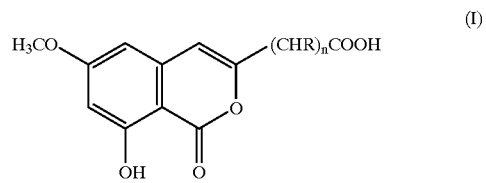

wherein R is a hydrogen atom or a $C_{1-6}$ alkyl group and n is an integer of 0 or 1, or a pharmaceutically acceptable salt thereof; and, in particular, such a pharmaceutical preparation useful for the prevention or treatment of diseases associated with an abnormality in immunological regulatory function or vascularization.

In another embodiment, the present invention provides the use of a compound of the above formula (I) or a pharmaceutically acceptable salt thereof, in the making of a pharmaceutical preparation for the prevention or treatment of diseases associated with an abnormality in immunological regulatory function or vascularization.

In still another embodiment, the present invention provides a method for the prevention or treatment of a disease associated with an abnormality in immunological regulatory function or vascularization, which comprises administering a pharmacologically effective amount of a compound of the above formula (I) or a pharmaceutically acceptable salt thereof to a mammal including a human being.

Moreover, as a novel compound among the compounds of the above formula (I), the present invention provides a compound of the formula (I-a)

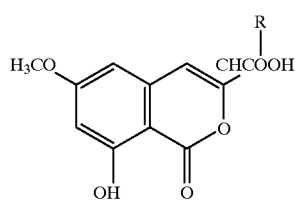

(I-a)

wherein R is a hydrogen atom or a $C_{1-6}$ alkyl group, or a salt thereof.

Furthermore, the present invention provides a compound of the formula (II)

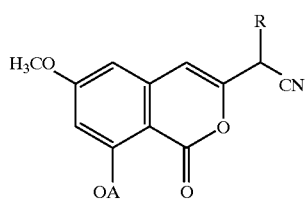

(II)

wherein R is a hydrogen atom or a $C_{1-6}$ alkyl group and A is a hydrogen atom or a protecting group, which can advantageously be used as an intermediate for the synthesis of the aforesaid compound of formula (I-a).

DETAILED DESCRIPTION OF THE INVENTION

Figure 1:
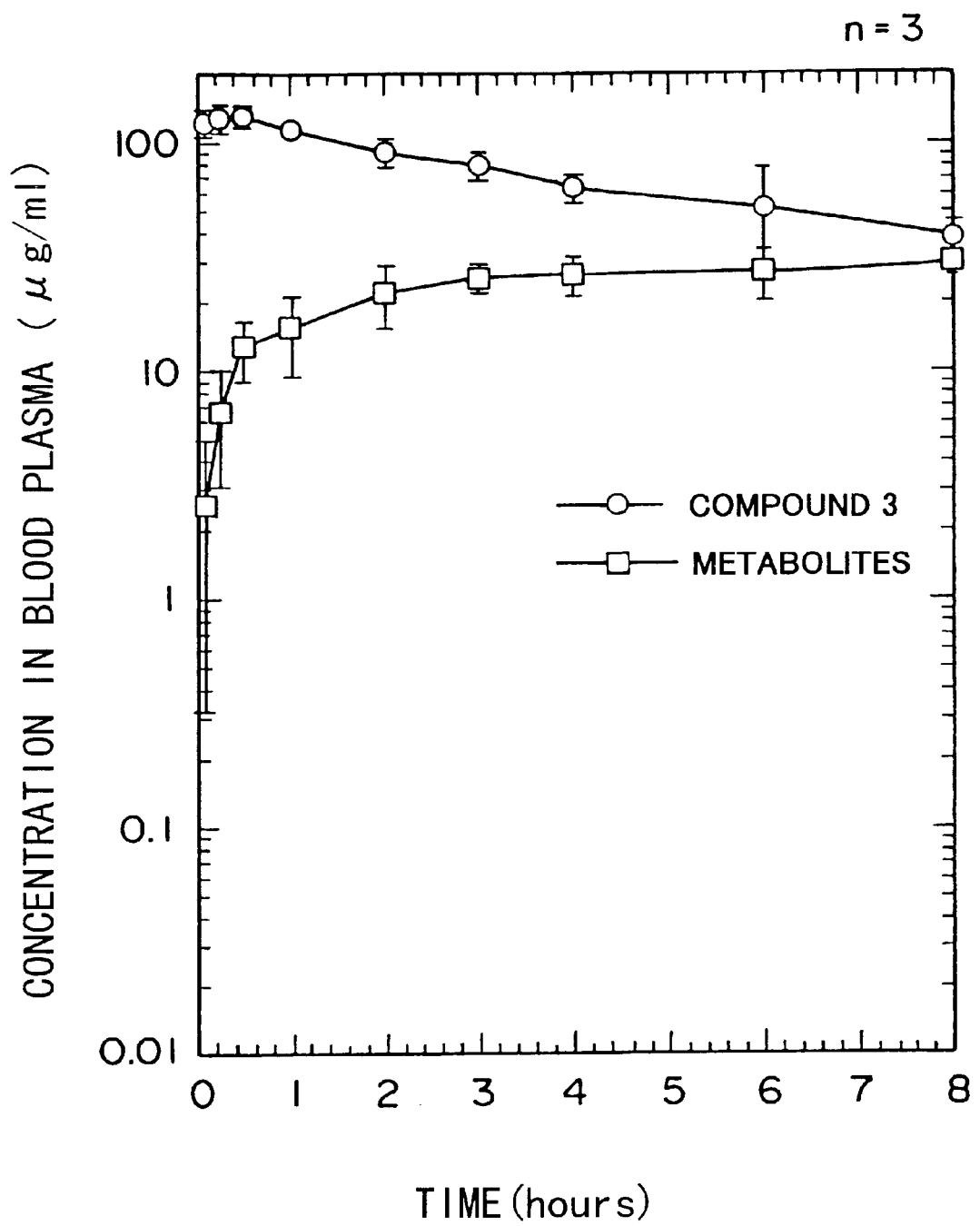
FIG. 1 is a graph showing changes with time of the concentrations of Compound 3 in accordance with the present invention and metabolites thereof in the blood plasma when this compound was orally administered to mice.

The compounds of formula (I) in accordance with the present invention are particularly characterized in that a carboxyl group is attached to the 3-position of an isocoumarin skeleton, either directly or indirectly via only one carbon atom constituting a methylene group (in which R is a hydrogen atom) or a methine group (in which R is a $C_{1-6}$ alkyl group). Where R is a $C_{1-6}$ alkyl group, specific examples of the alkyl group include methyl, ethyl, n- or isopropyl, n-, iso-, sec- or t-butyl, n-pentyl, isoamyl and n-hexyl. Where R is an alkyl group as described above, the compounds of formula (I) tend to show, in particular, an improvement in bioavailability (e.g., in vivo stability) and hence have higher usefulness in oral administration.

The specific compounds which can be used in the present invention are shown in the following table. In referring to compounds in accordance with the present invention, they may be designated by their respective Compound Nos.

TABLE

Specific Examples of the Compounds

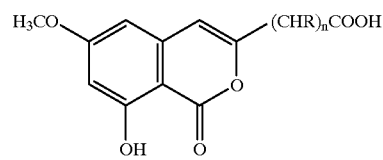

(I)

| Compound No. | n | R |
|---|---|---|
| 1 | 0 | — |
| 2 | 1 | H |
| 3 | 1 | $CH_3$ |
| 4 | 1 | $CH_2CH_3$ |
| 5 | 1 | $(CH_2)_2CH_3$ |
| 6 | 1 | $(CH_2)_2CH_3$ |
| 7 | 1 | $CH_2CH(CH_3)_2$ |
| 8 | 1 | $(CH_2)_4CH_3$ |
| 9 | 1 | $(CH_2)_2CH(CH_3)_2$ |
| 10 | 1 | $(CH_2)_5CH_3$ |
| 11 | 1 | $(CH_2)_3CH(CH_3)_2$ |

The above-described compounds of formula (I) may be used in the form of salts formed by the reaction of the carboxyl group with a basic compound. Any salts may be used, so long as they exert no adverse influence on the purpose of the present invention. However, it is preferable to use salts formed with basic compounds which are used to form pharmaceutically acceptable salts of common carboxyl-containing drugs. Specific examples of such salts include, but are not limited to, salts formed with alkali metals such as lithium, sodium and potassium; alkaline earth metals such as calcium and magnesium; and organic bases such as methylamine, ethylamine, dimethylamine, trimethylamine, triethylamine, pyridine, piperazine and piperidine.

Among the compounds in accordance with the present invention, Compound 1 is a known compound which has been isolated as a metabolite derived from *Aspergillus ochraceus* [Yamazaki et al., Chem. Pharm. Bull., 20(10), 2276–2278 (1972)]. However, this compound may also be prepared, for example, according to the following Reaction Scheme I.

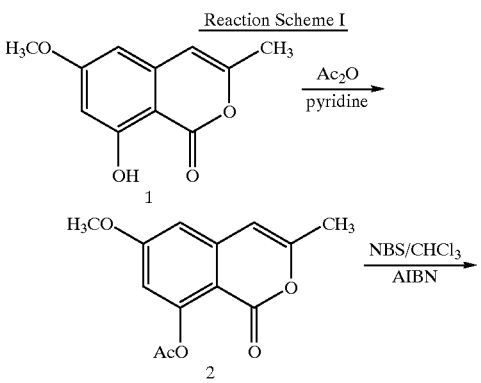

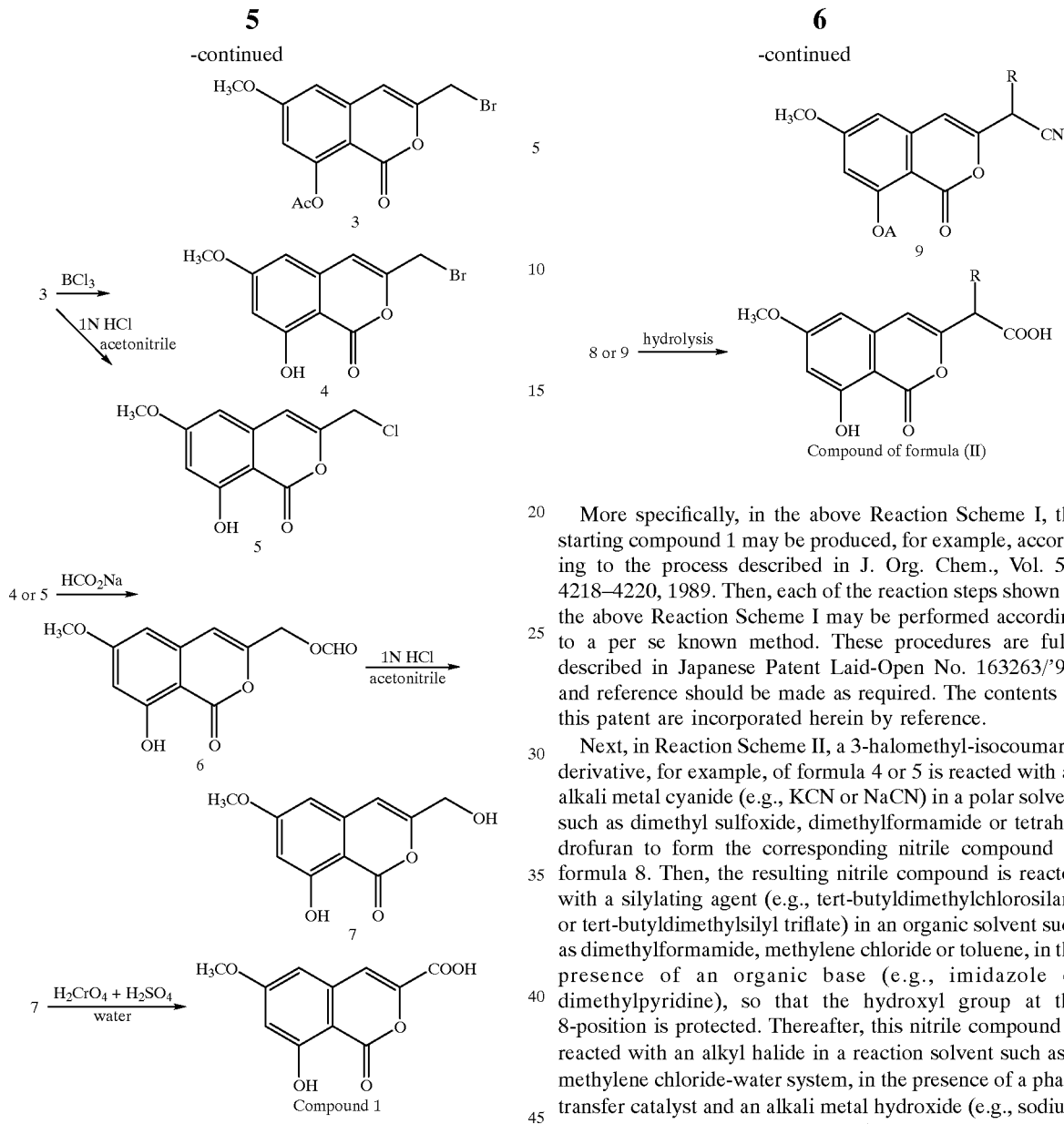

Moreover, the novel compounds of formula (II) may be prepared, for example, according to the following Reaction Scheme II.

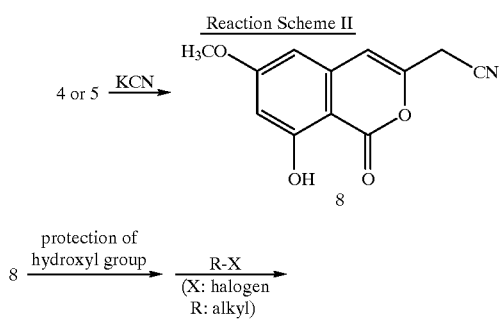

More specifically, in the above Reaction Scheme I, the starting compound 1 may be produced, for example, according to the process described in J. Org. Chem., Vol. 54, 4218–4220, 1989. Then, each of the reaction steps shown in the above Reaction Scheme I may be performed according to a per se known method. These procedures are fully described in Japanese Patent Laid-Open No. 163263/'93, and reference should be made as required. The contents of this patent are incorporated herein by reference.

Next, in Reaction Scheme II, a 3-halomethyl-isocoumarin derivative, for example, of formula 4 or 5 is reacted with an alkali metal cyanide (e.g., KCN or NaCN) in a polar solvent such as dimethyl sulfoxide, dimethylformamide or tetrahydrofuran to form the corresponding nitrile compound of formula 8. Then, the resulting nitrile compound is reacted with a silylating agent (e.g., tert-butyldimethylchlorosilane or tert-butyldimethylsilyl triflate) in an organic solvent such as dimethylformamide, methylene chloride or toluene, in the presence of an organic base (e.g., imidazole or dimethylpyridine), so that the hydroxyl group at the 8-position is protected. Thereafter, this nitrile compound is reacted with an alkyl halide in a reaction solvent such as a methylene chloride-water system, in the presence of a phase transfer catalyst and an alkali metal hydroxide (e.g., sodium hydroxide or potassium hydroxide), so that a nitrile compound of formula 9 is formed. If necessary, the hydroxyl-protecting group at the 8-position of the isocoumarin skeleton may be eliminated. The foregoing reactions may usually be carried out at a temperature ranging from 0° C. to the reflux temperature of the solvent used.

The compounds of formulae 8 and 9 thus obtained, as well as the compounds obtained by eliminating the hydroxyl-protecting group therefrom, have not been described in the literature of the prior art and are useful, for example, as intermediates for the synthesis of the compounds of formula (II) in accordance with the present invention. Accordingly, in place of the aforesaid silyl group, other groups such as trimethylsilyl, acetyl, propionyl, benzoyl, methoxymethyl, methoxyethoxymethyl and benzyloxymethyl may be used as hydroxyl-protecting groups. The present invention also provides the compounds of formulae 8 and 9 having these protecting groups.

The formation of a compound of formula (II) from a compound of formula 8 or 9 may be effected, for example, by treating the compound of formula 8 or 9 at 50–150° C. for 1–20 hours with an organic acid such as p-toluenesulfonic acid or methanesulfonic acid, or an inorganic solvent such as hydrochloric acid, sulfuric acid or phosphoric acid. As a result of this reaction, the aforesaid compound undergoes not only the elimination of the hydroxyl-protecting group, but also the hydrolysis of the cyano group and hence its conversion into a carboxyl group.

A salt of the carboxylic acid derivative thus obtained may be formed by the per se known salt-forming reaction with the corresponding basic compound.

The above-described compounds of the present invention and pharmaceutically acceptable salts thereof have an inhibitory effect, for example, on collagen-induced arthritis, as will be more fully described later. Accordingly, they are considered to be useful for the prevention and treatment of diseases associated primarily with an abnormality in immunological regulatory function, including autoimmune diseases such as chronic rheumatism, systemic lupus erythematosus, systemic scleroma, periarteritis nodosa, ulcerative colitis and juvenile diabetes; malignant tumors; severe infectious diseases; and the like.

Moreover, they also have an inhibitory effect, for example, on vascularization induced by tumor cells in the mouse back subcutaneous transplantation method. Accordingly, they are considered to be applicable to the prevention and treatment of diseases associated primarily with vascularization, such as the growth and metastasis of malignant solid tumors, diabetic retinopathy, various chronic inflammatory diseases, psoriasis, vascularization accompanying keratoplasty, and arteriosclerosis.

In addition, as compared with MI43 that is known to have an immunological regulatory effect, the compounds of the present invention have higher stability in vivo. Especially in the case of oral administration, they exhibit excellent bioavailability including significantly high in vivo stability. Moreover, they can be effectively and safely used without causing any appreciable toxicity.

The compounds in accordance with the present invention may be used alone, for example, to make pharmaceutical preparations for the prevention or treatment of diseases associated with abnormalities in immunological regulatory function or vascularization. However, they may preferably be used in combination with pharmaceutically acceptable additives. Such additives include diluents and excipients which are commonly used in this technical field, such as fillers, extenders, binders, humectants, disintegrators, disintegration inhibitors, surfactants and lubricants. With respect to such pharmaceutical preparations, various dosage forms may be chosen according to the therapeutic purpose. Typical examples thereof include tablets, pills, powders, solutions, suspension syrups, emulsions, granules, capsules, suppositories and injections (solutions, suspensions, etc.). The especially preferable route of administration which permits the compounds in accordance with the present invention to exhibits their effects is recognized to be oral administration. Among the above-described dosage forms, therefore, dosage forms for oral administration are preferred.

In forming the compounds into tablets, a wide variety of conventionally known carriers may be used. They include, for example, excipients such as lactose, sucrose, sodium chloride, glucose, urea, starch, calcium carbonate, kaolin, crystalline cellulose and silica; binders such as water, ethanol, propanol, simple syrup, glucose solution, starch solution, gelatin solution, carboxymethylcellulose, shellac, methylcellulose, potassium phosphate and polyvinyl pyrrolidone; disintegrators such as dried starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch and lactose; disintegration inhibitors such as sucrose, cacao butter and hydrogenated oil; absorption accelerators such as quaternary ammonium bases and sodium lauryl sulfate; humectants such as glycerin and starch; adsorbents such as starch, lactose, kaolin, bentonite and colloidal silica, and lubricants such as purified talc, stearic acid salts, boric acid powder and polyethylene glycol.

If desired, such tablets may be coated in the usual manner to form sugar-coated tablets, gelatin-covered tablets, film-coated tablets, two-layer tablets and multilayer tablets. In forming the compounds into pills, a wide variety of carriers conventionally known in this technical field may be used. They include, for example, excipients such as glucose, lactose, starch, cacao butter, hardened vegetable oils, kaolin and talc; binders such as powdered acacia, powdered tragacanth, gelatin and ethanol; and disintegrators such as laminaran and agar.

In forming the compounds into suppositories, a wide variety of carriers conventionally known in this field may be used. They include, for example, polyethylene glycol, cacao butter, higher alcohols, esters of higher alcohols, gelatin and semisynthetic glycerides.

Where the compounds are formed into injectable solutions and suspensions, it is preferable that such solutions and suspensions be sterile and isotonic to blood. In preparing such solutions and suspensions, any of diluents commonly used in this field may be used. They include, for example, water, ethanol, propylene glycol, ethoxylated isostearyl alcohol, polyoxy-isostearyl alcohol and polyoxyethylene sorbitan fatty acid esters. In this case, the preparations may contain sodium chloride, glucose or glycerin in an amount sufficient to form an isotonic solution. Moreover, common solubilizing agents, buffer agents, soothing agents and the like may also be used therein. Furthermore, if desired, the preparations for oral administration may additionally contain colorants, preservatives, perfumes, flavors, sweeteners and the like, as well as other drugs.

No particular limitation is placed on the content of the aforesaid compounds of the present invention in the pharmaceutical preparations in accordance with the present invention, and their content may vary widely. In the case of solid preparations such as tablets, granules and capsules, the content of the compounds of the present invention may usually be in the range of 1 to 70% by weight, preferably 5 to 50% by weight, based on the total composition. In the case of liquid preparations such as solutions, injections and suspensions, it may be in the range of 0.1 to 10% by weight.

No particular limitation is placed on the method for administering the compounds of the present invention, and they may suitably be administered according to the form of the preparation, the age, sex and other conditions of the patient, the degree of the disease, and the like. For example, in the case of tablets, pills, solutions, suspension syrups, emulsions, granules and capsules, they are administered orally. Although oral administration is preferred as described above, they may be intravenously administered as injections, either alone or in admixture with a common glucose or amino acid solution for infusion. If necessary, they may also be intramuscularly, intracutaneously, subcutaneously or intraperitoneally administered alone. In the case of suppositories, they are administered intrarectally.

The dosage of the compounds of the present invention may suitably be increased or decreased according to the method of administration, the age, sex and other conditions of the patient, the degree of the disease, and the like. However, in order to achieve a pharmacologically effective level in the body of the animal to which they are administered, they are suitably used, for example, in a daily dose of 0.3 to 300 mg/kg body weight for oral administration and 0.03 to 30 mg/kg body weight for parenteral administration.

Among the compounds in accordance with the present invention, each of Compounds 1, 2 and 3 was orally or intraperitoneally administered to eight DBA/1J mice in a dose of 100 mg/kg body weight. No animal died, and no animal showed evidences of toxicity. This seems to indicate that the compounds used in the present invention have no or very little, if any, acute toxicity. Moreover, Compound 1, in a dose of 100 mg/kg body weight, or Compound 3, in a dose of 30 mg/kg body weight, was orally administered to eight mice of the aforesaid strain for 40 days. No animal died, and no animal showed evidences of toxicity. Thus, the compounds of the present invention have little subacute toxicity. Since other compounds in accordance with the present invention are estimated to have similar properties, the compounds of the present invention can be used very safely.

Furthermore, as will be more specifically described later, the compounds in accordance with the present invention exhibit a marked effect in tests using model animals for chronic rheumatism and model animals for vascularization. On the other hand, they exhibit no inhibitory (or suppressive) effect on other enzymes induced by inflammation, such as cyclooxygenase (or prostaglandin endoperoxide synthase) and lipoxygenase, or on carrageenin edema serving as a model for acute inflammation. Accordingly, the pharmaceutical preparations of the present invention are characterized by a highly selective action and effect. In addition, as will be more specifically described later, the compounds in accordance with the present invention show a high concentration in the blood for 8 hours when they are orally administered to mice, and hence have excellent properties especially for use as oral drugs.

The present invention is more specifically explained with reference to the following examples. However, these examples are not to be construed to limit the scope of the invention.

Action and Effects
Inhibitory Effect on Collagen-Induced Arthritis (No. 1)

The preventive effect on the onset of collagen-induced arthritis was tested by using DBA/1J mice in groups of 5–8. Specifically, type II collagen was mixed with an equal volume of Freund's complete adjuvant and emulsified to prepare a 1 mg/ml emulsion. Mice were sensitized by administering 0.1 ml of this emulsion intracutaneously to the root of the tail. After 21 days, the mice were additionally immunized by emulsifying type II collagen in the same manner as before and administering 0.1 ml of the emulsion intraperitoneally so as to induce arthritis.

Starting from the day of the first sensitization with type II collagen, Compound 1 was orally administered, once a day, for 43 days in a dose of 10 or 30 mg/kg body weight. Similarly, each of Compounds 2 and 3 was intraperitoneally administered, once a day, for 43 days in a dose of 1 or 10 mg/kg body weight. Their inhibitory effect on collagen-induced arthritis was evaluated by measuring the sole thicknesses of the hind legs periodically with digital vernier calipers. The results thus obtained are shown in Table 1.

TABLE 1

Inhibitory Effect on Collagen-induced Arthritis No. 1

| Test compound | Dose (mg/kg/day) | Sole thickness (sum of left and right, mm), after 37 days |
|---|---|---|
| Control (no treatment) | — | 8.02 ± 0.82 |
| Compound 1 | 10 | 6.44 ± 0.40** |
|  | 30 | 6.12 ± 0.22** |
| Compound 2 | 1 | 6.81 ± 1.07* |
|  | 10 | 7.19 ± 0.40* |
| Compound 3 | 1 | 7.08 ± 0.16* |
|  | 10 | 6.78 ± 0.98* |

Mean ± standard deviation
Significantly different from the control group:
*$p < 0.05$;
**$p < 0.01$ Inhibitory Effect on Collagen-Induced Arthritis (No. 2)

Animals having arthritis induced in the same manner as described above were used in groups of 7–8. Compound 3 was orally administered, once a day, for 21 days following the additional immunization in a dose of 1, 3 or 10 mg/kg body weight. For comparative purposes, MI43 was similarly administered to another group in a dose of 30 mg/kg body weight. According to the degree of rubor, swelling and rigidity in each of the forelegs and hind legs of the experimental animals, their inhibitory effect on collagen-induced arthritis was evaluated on the following basis by a score ranging from 0 to 4 (with a maximum value of 16).

Score

0: No symptom is observed.

1: Only one of the small joints such as those of the fingers of the leg shows rubor and swelling.

2: Two or more small joints, or a relatively large joint such as that of the wrist or ankle, show rubor or swelling.

3: The hand or foot shows total rubor and swelling.

4: The total swelling of the hand or foot reaches its peak and, moreover, is accompanied by joint rigidity.

The results thus obtained are summarized in Table 2 below.

TABLE 2

Inhibitory Effect on Collagen-induced Arthritis No. 2

| Test compound | Dose (mg/kg/day) | Score after 37 days |
|---|---|---|
| Control (no treatment) | — | 9.25 ± 1.35 |
| Compound 3 | 1 | 6.50 ± 1.49 |
|  | 3 | 5.00 ± 1.61 |
|  | 10 | 3.50 ± 0.63** |
| MI43 (for comparison) | 30 | 5.29 ± 1.77 |

Mean ± standard error
Significantly different from the control group:
**p < 0.01

It can be seen from the above tables that the compounds in accordance with the present invention inhibited collagen-induced arthritis significantly. Moreover, in the case of oral administration, the administration of the compound in accordance with of the present invention reduced the arthritis score significantly even at a dose level of 30 mg/kg body weight, notwithstanding the fact that the administration of the comparative compound (MI43) in a dose of 30 mg/kg body weight caused no significant reduction in arthritis score.

Inhibitory Effect on Vascularization Using the Mouse Back Subcutaneous Transplantation Method The inhibitory effect of Compounds 1 and 3 in accordance with the present invention on the neogenesis of tumor vessels induced by the transplanted mouse tumor S180 was tested using the mouse back subcutaneous transplantation method. Specifically, $1 \times 10^7$ S180 cells were injected into a chamber formed by attaching a Millipore filter having a pore size of 0.45 μm to either side of a Millipore ring. After the injection hole was stopped up, this chamber was transplanted into an air sac formed beneath the skin of the back of a male ICR mouse (9–10 weeks old). Starting from the day of transplantation, a test compound or a solvent control comprising a 0.5% carboxymethylcellulose solution was orally administered for 5 days. After the skin was separated on the fifth day of transplantation, an O-ring of 10 mm internal diameter having the same shape as the Millipore ring was placed on the part of the skin which had been in contact with the chamber, observed under a stereoscopic microscope, and photographed.

In the photographs so taken, the degree of vascularization was rated 0, 1, 2 or 3 according to the number of 3 mm or longer tortuous blood vessels characteristic of tumoral vessels, and scored on the following basis.

Score

0: No tumoral vessel was observed.

1: One tumoral vessel was observed.

2: Two tumoral vessels were observed.

3: Three or more tumoral vessels were observed.

The results obtained with Compound 1 are shown in Table 3 below.

TABLE 3

Inhibitory Effect of Compound 1 on Vascularization Using the Mouse Back Subcutaneous Transplantation Method

| Vascularization score (mean ± standard error) | n | Significance level |
|---|---|---|
| A | 0.33 ± 0.17 | 9 | p < 0.001 |
| B | 3.00 ± 0.00 | 9 | p < 0.05 |
| C | 1.67 ± 0.53 | 9 | |

A: Phosphate buffer injection group (normal group).
B: (S180 tumor cell injection + solvent administration) group (control group).
C: [S180 tumor cell injection + Compound 1 (100 mg/kg body weight) administration] group.

The results obtained with Compound 3 are shown in Table 4 below.

TABLE 4

Inhibitory Effect of Compound 3 on Vascularization Using the Mouse Back Subcutaneous Transplantation Method

| Vascularization score (mean ± standard error) | n | Significance level |
|---|---|---|
| A | 0.27 ± 0.27 | 11 | ** |
| B | 2.93 ± 0.07 | 14 | |
| C | 2.40 ± 0.4 | 10 | * |
| D | 1.55 ± 0.43 | 11 | ** |
| E | 0.86 ± 0.33 | 14 | ** |
| F | 0.86 ± 0.38 | 14 | ** |
| G | 1.09 ± 0.39 | 11 | |

A: Phosphate buffer injection group (normal group).
B: (S180 tumor cell injection + solvent administration) group (control group).
C: [S180 tumor cell injection + Compound 3 (0.3 mg/kg) administration] group.
D: [S180 tumor cell injection + Compound 3 (1.0 mg/kg) administration] group.
E: [S180 tumor cell injection + Compound 3 (3 mg/kg) administration] group.
F: [S180 tumor cell injection + Compound 3 (10 mg/kg) administration] group.
G: [S180 tumor cell injection + MI43 (100 mg/kg) administration] group (for comparison).
*p < 0.05; **p < 0.01 (Student's t test)

It can be seen from the above Tables 3 and 4 that the oral administration of Compound 1 in a dose of 100 mg/kg body weight and Compound 3 in a dose of 1–10 mg/kg body weight significantly inhibited vascularization induced by the tumor cell S180 using the mouse back subcutaneous transplantation method.

Levels of Orally Administered Test Compounds in Blood Plasma

Each of Compound 3 and MI43 was orally administered to fasted male ICR mice (weighing 18–21 g) in a dose of 25 mg/kg. Blood samples were collected from the mice 5 minutes, 30 minutes, 4 hours, 8 hours and 24 hours after administration (3 mice per point for Compound 3 and 5 mice per point for MI43). These blood samples were centrifuged to obtain blood plasma samples. Each of the blood plasma samples was subjected to the following pretreatment and then analyzed by high-performance liquid chromatography (HPLC). 1.8 ml of a saturated aqueous solution of ammonium sulfate and 1.0 ml of methanol were added to and mixed with 0.2 ml of the blood plasma sample. This mixture was shaken with 3.5 ml of ethyl acetate. After this mixture was centrifuged, the ethyl acetate layer was separated. Moreover, the aqueous layer was shaken with 3.5 ml of ethyl acetate, followed by centrifugation. The ethyl acetate layer thus obtained was combined with the previously separated ethyl acetate layer, and this mixture was evaporated to dryness under reduced pressure. The resulting residue was redissolved in 0.2 ml of a 50% aqueous solution of acetonitrile and used as a sample for HPLC.

The analytical conditions for HPLC (using the CCTD system manufactured by Toso Co., Ltd.) were as follows: A YMC A-312 column (ODS 6×150 mm; manufactured by YMC Co., Ltd.) was used as the column. As the mobile phase, a 60:40 mixture of acetonitrile and 0.1% aqueous TFA was used for Compound 3, and a 40:60 mixture of acetonitrile and 0.1% aqueous TFA was used for MI43. The rest compound was eluted at a flow velocity of 1.0 ml/min and detected by UV light at 244 nm.

Figure 2:
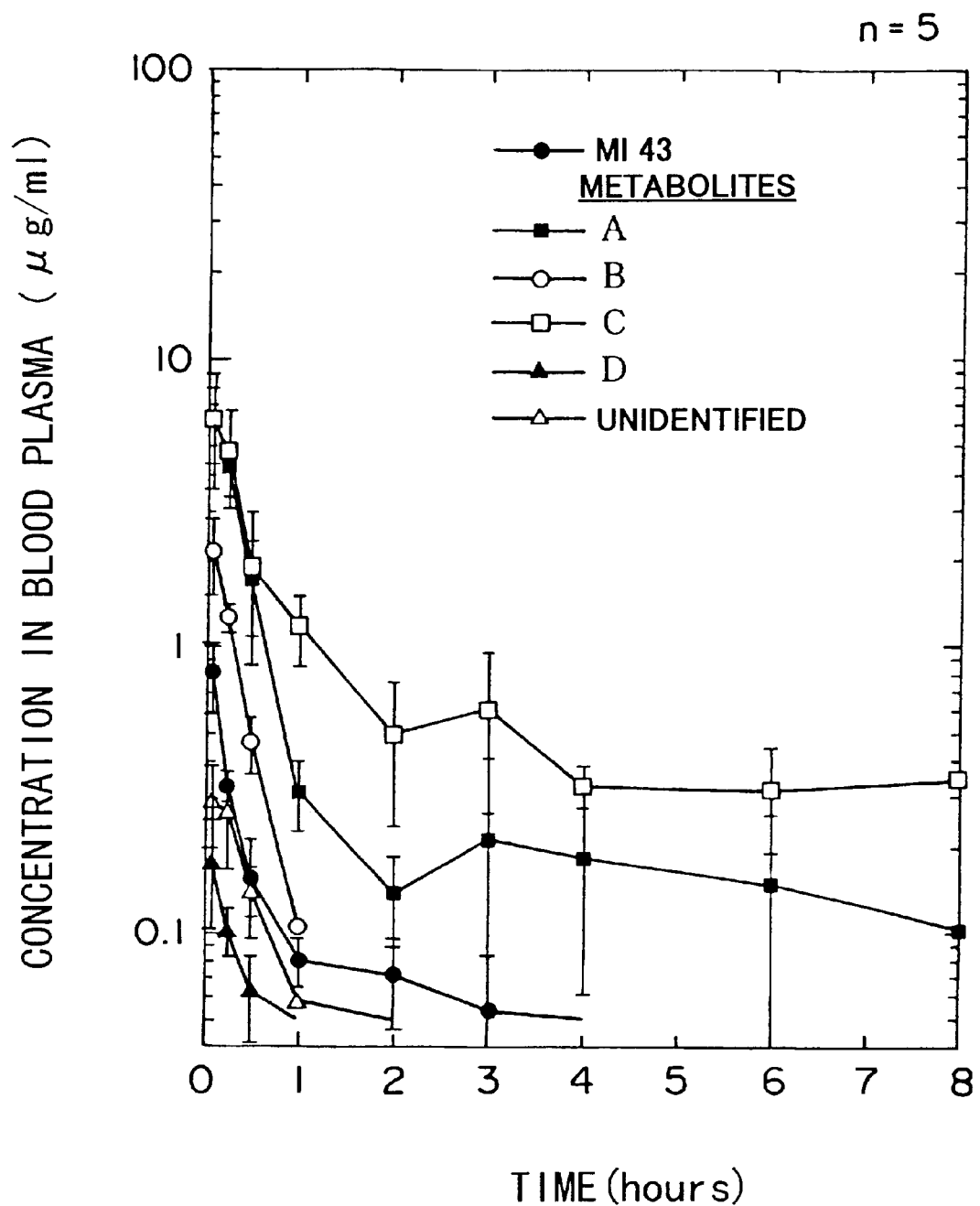
FIG. 2 is a graph showing changes with time of the concentrations of MI43 (as a comparative compound) and metabolites thereof in the blood plasma when this compound was orally administered to mice.

The concentrations of Compound 3 and MI43 in the blood plasma are shown in Tables 5 and 6, and their changes with time are shown in FIGS. 1 and 2. Unchanged Compound 3 reached a peak 30 minutes after administration, and then decreased. Its concentration in the blood plasma remained high even after 8 hours, but dropped to a vary low level after 24 hours. On the other hand, unchanged MI43 showed the highest level after 5 minutes, and then decreased sharply. In addition, 5 metabolites of MI43 were detected.

TABLE 5

Concentration of Compound 3 in Blood Plasma

| | µg/ml Time | | | | |
|---|---|---|---|---|---|
| | 5 (min) | 30 (min) | 4 (hr) | 8 (hr) | 24 (hr) |
| (Concentration of unchanged Compound 3) | | | | | |
| Mean | 122.54 | 131.34 | 63.01 | 38.41 | 0.19 |
| Standard deviation | 16.11 | 14.01 | 8.44 | 6.87 | 0.12 |
| (Unidentified metabolites) | | | | | |
| Mean | 2.61 | 12.78 | 26.28 | 30.29 | 0.80 |
| Standard deviation | 2.29 | 3.78 | 5.12 | 4.19 | 0.36 |

TABLE 6

Concentration of M143 for Comparison in Blood Plasma

| | (µg/ml) Time | | | |
|---|---|---|---|---|
| | 5 (min) | 30 (min) | 4 (hr) | 8 (hr) |
| (Concentration of unchanged M143) | | | | |
| Mean | 0.811 | 0.155 | 0.048 | — |
| Standard deviation | 0.225 | 0.059 | 0.016 | — |
| Metabolite A | | | | |
| Mean | 6.23 | 1.71 | 0.184 | 0.102 |
| Standard deviation | 2.68 | 0.622 | 0.123 | 0.076 |
| Metabolite B | | | | |
| Mean | 2.15 | 0.466 | — | — |
| Standard deviation | 0.637 | 0.106 | — | — |
| Metabolite C | | | | |
| Mean | 6.14 | 1.91 | 0.392 | 0.345 |
| Standard deviation | 1.795 | 1.045 | 0.055 | |

TABLE 6-continued

Concentration of M143 for Comparison in Blood Plasma

| | (µg/ml) Time | | | |
|---|---|---|---|---|
| | 5 (min) | 30 (min) | 4 (hr) | 8 (hr) |
| Metabolite D | | | | |
| Mean | 0.177 | 0.063 | — | — |
| Standard deviation | 0.074 | 0.021 | — | — |
| Unidentified metabolite | | | | |
| Mean | 0.292 | 0.142 | — | — |
| Standard deviation | 0.093 | 0.028 | — | — |

Metabolite A: A compound converted so as to have a —COOH at the 3-position.
Metabolite B: A compound having sulfuric acid conjugated with the hydroxyl group at the 8-position.
Metabolite C: A compound having glucuronic acid conjugated with the hydroxyl group at the 8-position.
Metabolite D: A compound converted so as to have a —OH at the 6-position.
—: Below detection limit.

Effect on Carrageenin Edema

The effect on carrageenin edema was tested by using ICR mice in groups of 6–7. Specifically, Compound 3 was orally administered thereto in a dose of 3 or 30 mg/kg body weight. As a positive control drug, indomethacin was similarly administered in a dose of 20 mg/kg body weight. After 30 minutes, 25 µl of a 1% carrageenin solution was subcutaneously injected into the sole of the right hind leg. Two hours after the administration of carrageenin, the thickness of the sole was measured with digital vernier calipers, and the degree of edema (%) based on the thickness measured before administration was calculated. The results thus obtained are shown in Table 7.

TABLE 7

Effect on Carrageenin Edema

| Test Compound | Dose (mg/kg) | Degree of edema (%) |
|---|---|---|
| Control (5% carboxy-methylcellulose solution) | — | 47.4 ± 2.8 |
| Compound 3 | 3 | 41.7 ± 3.1 |
| | 30 | 46.1 ± 4.2 |
| Indomethacin | 20 | 18.5 ± 3.5** |

Mean ± standard error
Significantly different from the control group: **p < 0.01

$$\text{Degree of edema }(\%) = \frac{(\text{Thickness after administration}) - (\text{Thickness before administration})}{(\text{Thickness before administration})} \times 100$$

It can be seen from the above table that Compound 3, when administered in doses of 3 and 30 mg/kg, had no inhibitory effect on carrageenin edema. In contrast, indomethacin, an anti-inflammatory agent, exhibited a significant inhibitory effect at a dose level of 20 mg/kg.

Effect on Cyclooxygenase and Lipoxygenase

The inhibitory effect of Compound 3 on cyclooxygenase (or prostaglandin endoperoxide synthase) activity was tested according to the method of Evans et al. (Biochemical Pharmacology, 36: 2035–2037, 1987). Specifically, an enzyme preparation derived from the seminal vesicles of sheep was incubated at 27° C. for 1.5 minutes in the presence of 500 μM arachidonic acid and 300 μM Compound 3. After the reaction was stopped by adding trichloroacetic acid to the reaction mixture, its absorbance was measured at 532 nm.

Moreover, its inhibitory effect on 5-lipoxygenase was tested according to the method of Egan et al. (Journal of Biological Chemistry, 260: 11554–11559, 1985). Specifically, an enzyme preparation derived from the basophilic leukemia cells (RBL-1) of rats was used. This enzyme preparation, together with 30 μM Compound 3, was incubated at room temperature for 5 minutes, followed by the addition of linolenic acid. Thereafter, this mixture was incubated at room temperature for 8 minutes. After the reaction was stopped by the addition of a sodium hydroxide solution, its absorbance was measured at 234 nm.

The results thus obtained are shown in Table 8 below.

TABLE 8

Effect on Cyclooxygenase and Lipoxygenase Activities

| Test compound | Degree of inhibition (%) | |
| --- | --- | --- |
| | Cyclooxygenase | 5-Lipoxygenase |
| Compound 3 | −4.0 | 21.0 | n = 2

It can be seen from the above table that Compound 3, used at a concentration of 30 μM or 300 μM, had no inhibitory effect on cyclooxygenase or lipoxygenase.

PREPARATION EXAMPLES

Example 1

Preparation of 8-hydroxy-6-methoxy-1-oxo-1H-2-benzopyran-3-carboxylic Acid (Compound 1)

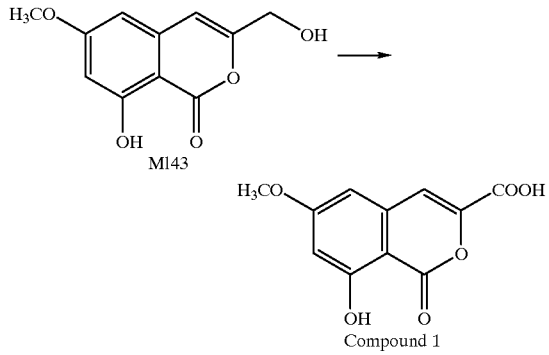

3.60 g (16.20 mmol) of MI43 was dissolved in 100 ml of acetone, and 14 ml of Jones' reagent was added thereto under cooling with ice. The resulting mixture was stirred at 0° C. for 10 minutes. After the addition of 500 ml of water, the reaction mixture was extracted with 1,000 ml and 500 ml portions of ethyl acetate. The organic layer was washed three times with 200 ml portions of a 20% aqueous solution of sodium chloride. The aqueous layer was re-extracted with 200 ml of ethyl acetate, and the resulting extract was washed twice with 100 ml portions of a 20% aqueous solution of sodium chloride. After the primary and secondary extracts were combined, this mixture was back-extracted four times with 300 ml portions of a 5% aqueous solution of sodium hydrogen carbonate. After water was added to make a total volume of 1,400 ml, the extract was adjusted to pH 3.0 with concentrated hydrochloric acid. The resulting white precipitate was collected by filtration, dried in vacuo, and dissolved in hot acetone. This solution was filtered to remove any insoluble matter, and the filtrate was concentrated. The resulting solid was suspended in 40 ml of a 10% aqueous solution of methanol, heated under reflux for 10 minutes, and then cooled with ice. The white crystals so formed were filtered off and dried under reduced pressure to obtain 2.36 g of Compound 1 in a 62% yield.

$^1$H-NMR spectrum (400 MHz, DMSO-$d_6$): The principal absorption peaks are as follows. δTMS (ppm): 3.88 (3H, s), 6.70 (1H, d, J=2.0 Hz), 6.95 (1H, d, J=2.0 Hz), 7.59 (1H, s), 10.98 (1H, s).

Example 2

Preparation of 3-chloromethyl-8-hydroxy-6-methoxy-1-oxo-1H-2-benzopyran

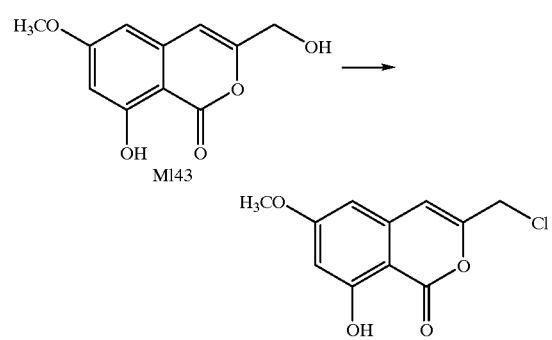

5.00 g (22.50 mmol) of MI43 and 10.0 g (38.25 mmol) of triphenylphosphine were dissolved in 50 ml of tetrahydrofuran. 30 ml (244 mmol) of carbon tetrachloride was added thereto, and the resulting mixture was heated under reflux for 30 minutes. After the reaction mixture was concentrated under reduced pressure, 18.46 g of the resulting residue was dissolved in 47 ml of ethanol and then recrystallized to obtain 4.72 g of the title compound in an 87% yield.

$^1$H-NMR spectrum (400 MHz, CDCl$_3$): The principal absorption peaks are as follows. δTMS (ppm): 3.88 (3H, s), 4.33 (2H, s), 6.40 (1H, d, J=2.4 Hz), 6.51 (1H, s), 6.53 (1H, d, J=2.4 Hz), 11.00 (1H, s).

Example 3

Preparation of 3-cyanomethyl-8-hydroxy-6-methoxy-1-oxo-1H-2-benzopyran

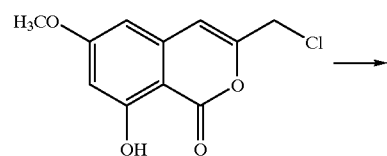

-continued

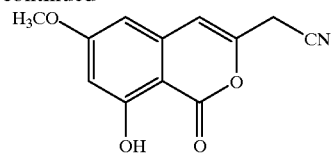

5.00 g (20.78 mmol) of the 3-chloromethyl-8-hydroxy-6-methoxy-1-oxo-1H-2-benzopyran obtained in Example 2 was dissolved in 70 ml of dimethyl sulfoxide. 4.29 g (83.11 mmol) of sodium cyanide was added thereto, and the resulting mixture was stirred under an atmosphere of nitrogen at 15° C. for 30 minutes. After the addition of 300 ml of water, the reaction mixture was extracted with 600 ml and 250 ml×3 portions of ethyl acetate. The organic layer was washed three times with 200 ml portions of a 20% aqueous solution of sodium chloride, dried over anhydrous sodium sulfate, and concentrated to about 300 ml under reduced pressure. After the addition of 3 g of activated carbon, this solution was heated under reflux for 10 minutes. The activated carbon was removed by filtration through Celite, and the filtrate and the washings were concentrated to about 100 ml. The precipitated crystals were dissolved by heating under reflux, and then cooled with ice. The reprecipitated crystals were filtered off to obtain 4.08 g of the title compound in an 84% yield.

$^1$H-NMR spectrum (400 MHz, DMSO-$d_6$): The principal absorption peaks are as follows. δTMS (ppm): 3.65 (2H, d, J=1.1 Hz), 3.89 (3H, s), 6.42 (1H, d, J=2.4 Hz), 6.54 (1H, d, J=2.4 Hz), 6.58 (1H, s), 10.82 (1H, s).

Example 4

Preparation of (8-hydroxy-6-methoxy-1-oxo-1H-2-benzopyran-3-yl)acetic Acid (Compound 2)

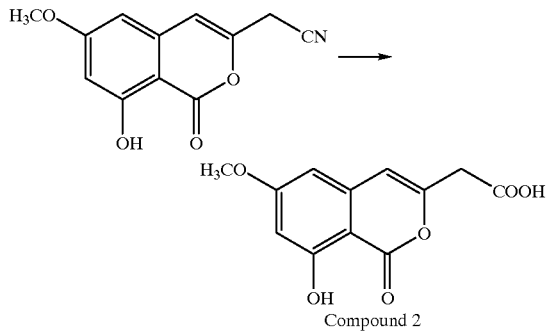

1.50 g (6.49 mmol) of the 3-cyano-8-hydroxy-6-methoxy-1-oxo-1H-2-benzopyran obtained in Example 3 was suspended in 8 ml of acetic acid and 8 ml of concentrated hydrochloric acid, and the resulting suspension was stirred at 70° C. for 5.5 hours. The reaction mixture was concentrated and extracted with 150 ml of ethyl acetate. The organic layer was washed three times with 50 ml portions of a 20% aqueous solution of sodium chloride, dried over anhydrous sodium sulfate, concentrated under reduced pressure, and dried in vacuo to obtain a black powder. 20 ml of ethanol and 0.3 g of activated carbon were added thereto, and the resulting mixture was heated under reflux for 30 minutes. After the activated carbon was removed, the white crystals formed upon cooling were filtered off and dried under reduced pressure to obtain 1.30 g of the title compound (Compound 2) in an 80% yield.

IR absorption spectrum (KBr): The characteristic absorption peaks are as follows (unit: cm$^{-1}$)

$v_{max}$: 1238, 1574, 1626, 1651, 1690, 1723.

$^1$H-NMR spectrum (400 MHz, DMSO-$d_6$): The principal absorption peaks are as follows. δTMS (ppm): 3.62 (2H, s), 3.86 (3H, s), 6.56 (1H, d, J=2.4 Hz), 6.63 (1H, d, J=2.4 Hz), 6.66 (1H, s), 10.90 (1H, s).

Example 5

Preparation of 8-tert-butyldimethylsilyloxy-3-cyanomethyl-6-methoxy-1-oxo-1H-2-benzopyran

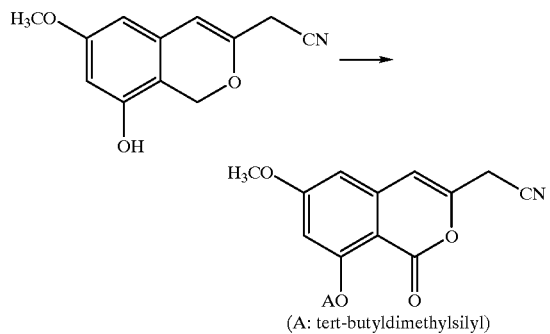

(A: tert-butyldimethylsilyl)

2.70 g (11.68 mmol) of the 3-cyanomethyl-8-hydroxy-6-methoxy-1-oxo-1H-2-benzopyran obtained in Example 3 was suspended in 25 ml of dimethylformamide. 1.59 g (23.4 mmol) of imidazole and 2.82 g (18.7 mmol) of tert-butyldimethylsilyl chloride were successively added thereto under cooling with ice, and the resulting mixture was stirred for 2 hours. After completion of the reaction, the reaction mixture was mixed with toluene, washed once with 50 ml of a 10% aqueous solution of sodium chloride, and washed twice with 50 ml portions of a 20% aqueous solution of sodium chloride. The toluene layer was dried over anhydrous sodium sulfate, concentrated under reduced pressure, and dried in vacuo. The resulting residue was recrystallized from 20 ml of ethanol to obtain 3.77 g of the title compound in a 93% yield.

$^1$H-NMR spectrum (400 MHz, CDCl$_3$): The principal absorption peaks are as follows. δTMS (ppm): 0.28 (6H, s), 1.05 (9H, s), 3.59 (2H, d, J=1.6 Hz), 3.87 (3H, s), 6.45 (3H, m).

Example 6

Preparation of 8-tert-butyldimethylsilyloxy-3-(1-cyanoethyl)-6-methoxy-1-oxo-1H-2-benzopyran

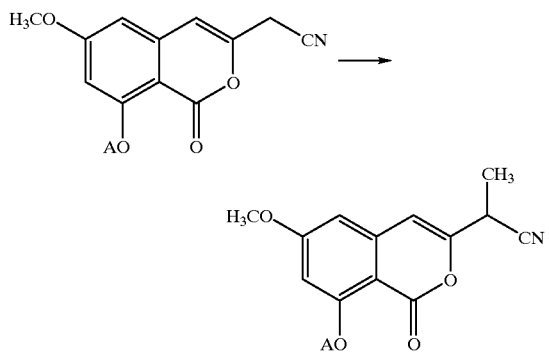

2.50 g (7.24 mmol) of the 8-tert-butyldimethylsilyloxy-3-cyanomethyl-6-methoxy-1-oxo-1H-2-benzopyran obtained in Example 5 was dissolved in 80 ml of methylene chloride. 100 ml of a 1M aqueous solution of sodium hydroxide was added thereto, and the resulting mixture was cooled to 0° C. While this mixture was being vigorously stirred, 584 mg (1.81 mmol) of tetrabutylammonium fluoride and then 10 ml of methylene chloride containing 0.92 ml (14.47 mmol) of methyl iodide were added thereto, followed by stirring at 0° C. for 1 hour. Moreover, 10 ml of methylene chloride containing 0.92 ml (14.47 mmol) of methyl iodide was added thereto, followed by stirring for 30 minutes. After completion of the reaction, the methylene chloride layer was separated, dried over anhydrous sodium sulfate, and concentrated under reduced pressure. The resulting residue was purified by silica gel column chromatography [using 130 g of Wako Gel C-200 and hexane/ethyl acetate (5:1)]. Thus, 1.01 g of the title compound was obtained in a 39% yield.

$^1$H-NMR spectrum (400 MHz, CDCl$_3$): The principal absorption peaks are as follows. δTMS (ppm): 0.28 (6H, s), 1.05 (9H, s), 1.68 (3H, d, J=7.2 Hz), 3.73 (1H, q, J=7.2 Hz), 3.87 (3H, s), 6.45 (1H, d, J=2.0 Hz), 6.46 (1H, d, J=2.0 Hz), 6.48 (1H, s).

Example 7

Preparation of 2-(8-hydroxy-6-methoxy-1-oxo-1H-2-benzopyran-3-yl)propionic Acid (Compound 3)

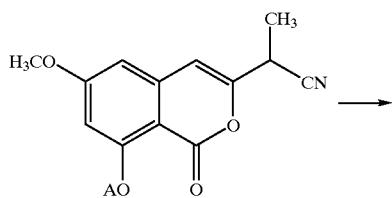

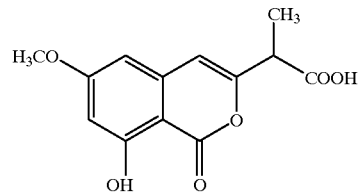

1.63 g (4.72 mmol) of the 8-tert-butyldimethylsilyloxy-3-(1-cyanoethyl)-6-methoxy-1-oxo-1H-2-benzopyran obtained in Example 6 was dissolved in 5 ml of acetic acid and 5 ml of concentrated hydrochloric acid, and the resulting solution was stirred at 70° C. for 12 hours. After the reaction mixture was cooled, 10 ml of water was added thereto so as to precipitate crystals. These crystals were collected by filtration, washed with water, and dried under reduced pressure to obtain 1.21 g of crude crystals of the title compound. After the addition of 8 ml of ethanol, the resulting mixture was heated under reflux and then cooled. The pale-yellow crystals so formed were filtered off and dried under reduced pressure to obtain 1.04 g of the title compound (Compound 3) in an 80% yield.

$^1$H-NMR spectrum (400 MHz, DMSO-d$_6$): The principal absorption peaks are as follows. δTMS (ppm): 1.40 (3H, d, J=7.2 Hz), 3.70 (1H, q, J=7.2 Hz), 3.86 (3H, s), 6.56 (1H, d, J=1.6 Hz), 6.67 (1H, d, J=1.6 Hz), 6.68 (1H, s), 10.90 (1H, s).

Example 8

Preparation of Capsules 20 mg of Compound 1 prepared in the manner described in Example 1, 180 mg of lactose, and 1 mg of magnesium stearate are intimately blended together (the amounts indicated are for one capsule). No. 3 hard gelatin capsules are filled with about 200 mg each of the resulting blend.

Example 9

Preparation of Tablets 10 mg of Compound 2 prepared in the manner described in Example 4, 120 mg of lactose, and 57 mg of corn starch are blended well (the amounts indicated are for one tablet). This blend is granulated by mixing it with a 10% starch paste solution, and the resulting granules are blended well with 60 mg of corn starch and 3 mg of magnesium stearate (the amounts indicated are for one tablet). The resulting blend is formed into tablets having a diameter of 8 mm and a weight of about 250 mg.

Example 10

Preparation of a Suspension Syrup 100 mg of Compound 3 prepared in the manner described in Example 7, 100 mg of carboxymethylcellulose sodium, 14 mg of methyl parahydroxybenzoate, 14 mg of ethyl parahydroxybenzoate, 40 ml of simple syrup, and 10 ml of purified water are mixed well to form a suspension (the amounts indicated are for one bottle). This suspension is poured in a dispensing bottle.

Exploitability in Industry

According to the present invention, there are provided compounds or pharmaceutical preparations having an excellent immunological regulatory effect and an excellent inhibitory effect on vascularization. Accordingly, the present invention is useful in the pharmaceutical industry.

We claim:

1. A pharmaceutical preparation comprising a pharmaceutically acceptable additive and a pharmacologically effective amount of a compound of the formula (I)

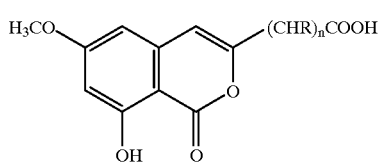

(I)

wherein R is a hydrogen atom or a $C_{1-6}$ alkyl group and n is an integer of 0 or 1, or a pharmaceutically acceptable salt thereof.

2. A pharmaceutical preparation as claimed in claim 1 wherein n is an integer of 1.

3. A pharmaceutical preparation as claimed in claim 1 which has a dosage form for oral administration.

4. A method for the treatment of a disease associated with an abnormality in immunological regulatory function or vascularization, which comprises administering a pharmacologically effective amount of a compound of the formula (I)

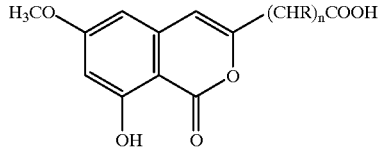

(I)

wherein R is a hydrogen atom or a $C_{1-6}$ alkyl group and n is an integer of 0 or 1, or a pharmaceutically acceptable salt thereof to a mammal.

5. A method as claimed in claim 4 wherein n is an integer of 1.

6. A method as claimed in claim 4 wherein the administration is oral administration.

7. A method as claimed in claim 4 wherein the disease is an autoimmune disease.

8. A method as claimed in claim 4 wherein n is an integer of 1, the administration is oral administration, and the disease is an autoimmune disease.

9. A compound of the formula (I-a)

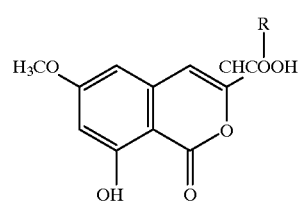

(I-a)

wherein R is a hydrogen atom or a $C_{1-6}$ alkyl group, or a salt thereof.

10. A compound of the formula (II)

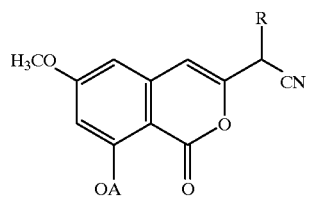

(II)

wherein R is a hydrogen atom or a $C_{1-6}$ alkyl group and A is a hydrogen atom or a protecting group.

* * * * *